United States Patent [19]

Kollar

[11] Patent Number: 5,321,157
[45] Date of Patent: Jun. 14, 1994

[54] PROCESS FOR THE PREPARATION OF ADIPIC ACID AND OTHER ALIPHATIC DIBASIC ACIDS

[75] Inventor: John Kollar, Wyckoff, N.J.

[73] Assignee: Redox Technologies Inc., Wyckoff, N.J.

[21] Appl. No.: 53,791

[22] Filed: Apr. 26, 1993

Related U.S. Application Data

[63] Continuation-in-part of Ser. No. 951,743, Sep. 25, 1992.

[51] Int. Cl.$^5$ ............................................. C07C 51/31
[52] U.S. Cl. .................................................. 562/543
[58] Field of Search ............... 562/543; 560/191, 204

[56] References Cited

U.S. PATENT DOCUMENTS

| | | | |
|---|---|---|---|
| 2,223,493 | 12/1940 | Loder | 260/537 |
| 2,589,648 | 3/1952 | Wadsworth | 260/533 |
| 3,231,608 | 1/1966 | Kollar | 260/533 |
| 3,390,174 | 6/1968 | Schulz et al. | 260/533 |
| 3,657,334 | 4/1972 | Kulrestha et al. | 260/531 R |
| 4,032,569 | 6/1977 | Onopchenko et al. | 260/533 C |
| 4,105,856 | 8/1978 | Newton | 560/191 |
| 4,158,739 | 6/1979 | Schulz et al. | 562/543 |
| 4,263,453 | 4/1981 | Schulz et al. | 562/543 |
| 4,331,608 | 5/1982 | Kawamoto et al. | 562/543 X |
| 4,606,863 | 8/1986 | Nakazawa et al. | 562/543 X |
| 4,902,827 | 2/1990 | Steinmetz et al. | 562/543 |
| 5,221,800 | 6/1993 | Park et al. | 562/543 |

FOREIGN PATENT DOCUMENTS 1304855  1/1973  United Kingdom .

OTHER PUBLICATIONS

Chemical Abstracts, Volume 93, No. 15, Abstract No. 149471g (1980).
Patents Abstracts of Japan, Vol. 7, No. 97 C-163, Abstract of JP A, 58-21642 (1983).
G. N. Kulsrestha et al. in J. Chem. Tech. Biotechnol., 50, 57-65 (1991).
K. Tanaka in Chemtech, 555-559 (1974).
Hydrocarbon Processing, 53, 114-120 (1974).

*Primary Examiner*—Arthur C. Prescott
*Attorney, Agent, or Firm*—Joseph C. Gil; Richard E. L. Henderson

[57] ABSTRACT

The present invention relates to a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen-containing gas mixture
   in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and (2) isolating the $C_5$–$C_8$ aliphatic dibasic acid.

13 Claims, No Drawings

PROCESS FOR THE PREPARATION OF ADIPIC ACID AND OTHER ALIPHATIC DIBASIC ACIDS

This application is a continuation-in-part of application Ser. No. 07/951,743, filed Sep. 25, 1992.

BACKGROUND OF THE INVENTION

The present invention relates to a process for the preparation of adipic acid and other lower aliphatic dibasic acids by the oxidation of saturated cyclic hydrocarbons.

Adipic acid is a major article of commerce and its preparation has, therefore, attracted much attention. Consequently, many processes for the production of adipic acid have been proposed. For example, one process involves nitric acid oxidation of cyclohexanol, cyclohexanone, or mixtures thereof, which can in turn be obtained by air oxidation of cyclohexane or hydrogenation of phenol. Several of these known processes are practiced commercially, but all suffer from high costs associated with such multi-step operations and the use of nitric acid, as well as from significant environmental pollution problems caused by the discharge of ozone-depleting nitrogen oxide by-products generated during nitric acid oxidation.

Processes that have been proposed for preparing dibasic acids without the use of nitric acid include air oxidation of saturated cyclic hydrocarbons and/or corresponding cyclic ketones and/or alcohols. For example, U.S. Pat. No. 3,390,174 and British Patent 1,304,855 disclose processes requiring mixtures of two or more of these components. However, many air oxidation processes are multi-step processes having poor selectivities and requiring difficult high-cost recovery processes. Nevertheless, an air oxidation process that provides good yields of a single dibasic acid free of significant by-products would be highly desirable.

Catalytic air oxidation processes are believed to involve free radical oxidation. Such oxidations are complex systems in which many types of reactions other than oxidation can occur. Free radicals will attack any C—H bonds, regardless of form, to an extent determined by bond strength and relative concentration of the specific C—H bond. As oxidation proceeds, various oxygenated compounds form, such as alcohols, aldehydes, ketones, and acids (including difunctional compounds having these functionalities), as well as other low molecular weight carbon compounds. All of these compounds can further react via acid catalysis or thermal ionic mechanisms to form various condensation products, the most prevalent being esters. In general, the amount of condensation products will increase as the rate of oxidation relative to ester formation decreases. Process modifications that improve the ratio of oxidation to ester formation would be expected to yield a greater amount of easily recoverable diacid. In addition, modifications that lower the rate of esterification would be expected to improve the amount of easily recoverable diacid.

Until now, however, the seemingly attractive direct oxidation routes have not provided a viable commercial process, possibly because of the complexity of the reaction residues ("bottoms") containing many different simple esters derived from the various intermediates, oxidation products, and post-oxidation products. Such complexity is not unique to saturated cyclic alkane oxidations. These complex reactions exist even for oxidations of aromatic compounds such as xylenes. The primary distinction is that bottoms from methyl-substituted aromatic oxidation (i.e., intermediates, derivatives, and the like) can be subjected to very stringent oxidation conditions that allow continued oxidation to oxidation-stable aromatic acids. For example, the aromatic acid products are extremely stable to further oxidation and can be subjected to extreme conditions under which a substantial amount of the seemingly inert acetic acid would be oxidized to $CO_2$ and water. Consequently, these aromatic acid products can be produced substantially free of oxidation bottoms, intermediates, derivatives, and the like at very high conversions of 95% or higher.

Aliphatic diacids such as adipic acid, on the other hand, are subject to further oxidation because the C—H bonds of the methylene groups in such acids can more readily undergo free radical attack and oxidation. If subjected to forcing oxidation conditions at higher conversion, the various bottoms, intermediates, and derivatives will oxidize (as do similar aromatic compounds). However, because of the relative instability to oxidation of the aliphatic acids (such as adipic, glutaric, and succinic acids, and even acetic acid under stringent conditions), these acid products will progressively and increasingly degrade to $CO_2$ and water, thereby providing lower selectivity.

It was, therefore, an object of the present invention to avoid these problems and achieve a chemical process having desirable commercial features.

Single-step direct air oxidation processes for the production of dibasic acids have also been proposed. However, previous one-step processes have been attended with poor selectivity, low production rate, multi-step operation, burdensome and costly separation, and low ultimate overall yields of dibasic acids from the saturated cyclic hydrocarbon. For example, U.S. Pat. No. 2,223,493 discloses a process for the direct oxidation of cyclohexane to form adipic acid at a reported production rate of 3.1 wt. % per hour in a concentration of 12.4 wt. % in the oxidation effluent with an overall selectivity of 46 to 49 mole %. This oxidation was carried out using a comparatively high concentration of cyclohexane (about 61 to 63 wt. %) in acetic acid solvent in the presence of air and various catalysts at temperatures of from 95° C. to 120° C. until a conversion level of about 23 to 24% was achieved.

U.S. Pat. No. 2,589,648 discloses a single-step oxidation process in which acetone is used instead of acetic acid as solvent.

U.S. Pat. No. 3,231,608 discloses another single-step direct oxidation process for the production of dibasic aliphatic acids. The reference teaches that the use of certain critical ratios of solvent and catalyst to the saturated cyclic hydrocarbon can yield dibasic aliphatic acids under mild reaction conditions, usually at production rates of adipic acid of 3.5 to 4.0 wt. % per hour and at efficiencies generally around 73 to 76 wt. %. In particular, the reference teaches that molar ratios of solvent to saturated cyclic hydrocarbon in the range of 1.5:1 to 7:1 (or more) are suitable but that molar ratios below or above this range give unsatisfactory results. A comparison example carried out using molar ratios more nearly like those of the present invention gave a decidedly inferior adipic acid production rate. The process of the present invention provides excellent results despite using molar ratios of solvent to cycloaliphatic hydrocarbon well below the range specified for the process disclosed in U.S. Pat. No. 3,231,608.

Additional references describe attempts to improve upon the process of U.S. Pat. No. 3,231,608. A general objective of these references was attainment of higher conversions of cyclohexane, which was usually achieved by lowering the starting concentration of cyclohexane, by using protracted reaction times, or by making other such changes, with the result being very low reaction rates, reduced selectivities, and expensive recovery and downstream processing. For example, U.S. Pat. Nos. 4,032,569 and 4,263,453 require a greater relative amount of cobalt(III) catalyst (and U.S. Pat. No. 4,263,453 requires small amounts of water) but still specify essentially the same molar ratios of solvent to cycloalkane as U.S. Pat. No. 3,231,608. G. N. Kulsrestha et al in *Chem. Tech. Biotechnol.*, 50, 57-65 (1991), similarly discloses an oxidation process that uses a relatively large excess of acetic acid and a large amount of cobalt(III) catalyst. U.S. Pat. No. 4,158,739 discloses a similar preparation of glutaric acid from cyclopentane in which the molar ratio of solvent to cyclopentane must be at least 1.5:1 and the amount of catalyst is relatively higher than for U.S. Pat. No. 3,231,608. In general, the use of excess acetic acid solvent at the higher molar ratios disclosed in the prior art appears to reduce the rate of adipic acid product.

Further details on a known single-stage oxidation process for the preparation of adipic acid from cyclohexane are discussed by K. Tanaka in *Chemtech*, 555-559 (1974), and *Hydrocarbon Processing*, 53, 114-120 (1974).

It has now surprisingly been found that, contrary to the expectations of the prior art, the oxidation of high concentrations of cycloalkanes at low conversion levels provides advantageous chemical and economic results. For example, use of high cyclohexane concentrations at restricted conversion levels, in conjunction with mild reaction conditions and with catalysts such as cobalt(II) or cobalt(III) ion that generate free radicals in an organic acid/or mixed solvent, gives a rapid rate of adipic acid production with minimal structural loss of $C_6$ compounds (that is, with lower conversion to $C_5$, $C_4$, or lower of carbon-containing by-products). The oxidation process of the invention permits a surprisingly facile recovery of adipic acid because of the strong tendency of the oxidation effluent upon cooling to separate cleanly into phases. The large non-polar upper phase can be directly recycled for oxidation without costly processing, whereas the polar lower phase is extremely rich in adipic acid that can be recovered in high yield by filtration or centrifugation, with the filtrate or supernatant can to a large degree be directly returned to oxidation without costly reprocessing.

SUMMARY OF THE INVENTION

Accordingly, the present invention relates to a process for the preparation of $C_5$-$C_8$ aliphatic dibasic acids by oxidation of corresponding saturated cycloaliphatic hydrocarbons comprising (1) reacting, at a cycloaliphatic hydrocarbon conversion level of between about 7% and about 30% (preferably between 10% and 30% and more preferably between 15% and 25%),
(a) at least one saturated cycloaliphatic hydrocarbon having from 5 to 8 ring carbon atoms in the liquid phase and
(b) an excess, relative to cycloaliphatic hydrocarbon (a), of oxygen gas or an oxygen-containing gas mixture in the presence of (c) less than 1.5 moles (preferably 0.1 to 1.0 moles) of a solvent per mole of cycloaliphatic hydrocarbon (a), wherein said solvent comprises an organic acid containing only primary and/or secondary hydrogen atoms and
(d) at least about 0.002 mole (preferably 0.015 to about 0.3 mole) per 1000 grams of reaction mixture of a polyvalent heavy metal catalyst (preferably comprising a cobalt salt of an organic acid); and
(2) isolating the $C_5$-$C_8$ aliphatic dibasic acid.

DETAILED DESCRIPTION OF THE INVENTION

Suitable cyclic hydrocarbons for use as component (a) of the invention include saturated cyclic hydrocarbons having from 5 to 8 ring carbon atoms and containing only primary and secondary hydrogen atoms. Examples of suitable saturated cyclic hydrocarbons include cyclopentane, cyclohexane, cycloheptane, cyclooctane, or hydrocarbon analogs or homologs thereof that contain only primary and secondary hydrogen atoms. A particularly preferred cyclic hydrocarbon is cyclohexane, which is a readily available commercial product.

Component (a) may also contain any substantially inert diluent, such as another hydrocarbon (other than a saturated cycloaliphatic hydrocarbon) containing only primary and secondary hydrogens. In general, however, such diluents are preferably removed, especially if present in larger amounts, because they necessarily occupy reactor space. A particularly beneficial inert diluent is benzene, the ultimate source of commercially produced cyclohexane. The presence of benzene can be economically advantageous for the production of adipic acid by enhancing the rate of oxidation and by allowing the use of lower grade cyclohexane from which benzene need not be removed.

In particular, when preparing adipic acid from cyclohexane according to the invention, the cyclohexane can contain substantial amounts of benzene without detrimental effect on the oxidation process. In fact, when benzene replaces a portion of solvent (c) (e.g., acetic acid), the rate of oxidation may even be improved. For example, it has been found that the presence of up to about 60% by weight of benzene relative to cyclohexane actually increases the oxidation rate.

In addition, cyclohexane is produced commercially by hydrogenation of benzene. The conditions for hydrogenation are generally harsh so as to optimize conversion and to minimize the cost associated with the difficult separation of benzene from the cyclohexane product. Thus, for example, the use of cyclohexane containing 0.1 wt. % (or less) up to 5 or 10 wt. % of benzene can reduce raw material costs. Consequently, the more favorable oxidation kinetics and less demanding distillation requirements would permit substantially greater production of cyclohexane from an existing cyclohexane facility.

The oxidant (b) used in the process of the invention can be essentially any gas containing free molecular oxygen and optional substantially inert gaseous diluents. Examples of suitable oxygen-containing gases are air and oxygen-enriched air (that is, air having an augmented oxygen content of, for example, 85 mole percent or more), as well as pure gaseous oxygen. A mixture of 50 wt. % oxygen and 50 wt. % nitrogen, for example, provides satisfactory results. Even oxygen-depleted air can be used but is less preferred. Any gases that are substantially inert under the reaction conditions are suitable gaseous diluents. Examples of such gaseous diluents include nitrogen, carbon dioxide, helium, neon and argon, as well as the normally gaseous paraffin hydrocarbons (such as methane, ethane, and propane). Mixtures of diluents can, of course, also be used. Regardless of the oxygen-containing gas used, the molar quantity of oxygen should be at least sufficient to provide complete oxidation of the cycloaliphatic hydrocarbon to the corresponding dibasic acid (that is, at least 2.5 moles of $O_2$ for each mole of cycloaliphatic hydrocarbon).

The partial pressure of oxygen over the reaction mixture should be at least 0.10 atmosphere absolute and can be as high as 100 atmosphere absolute, or even higher. The preferred partial pressure of oxygen over the reaction mixture should be from at least about 0.10 to about 0.30 atmospheres absolute. The total pressure should be at least sufficient to keep the reactants in the liquid phase. The total reaction pressure that is employed will depend to a large extent on the particular oxygen-containing gas which is used, the composition of the reacting mixture, and temperature, which together determine the vapor pressure of the liquid reacting mixture.

Suitable solvents for use as component (c) of the invention can be essentially any weak organic acids that contain only primary and/or secondary hydrogen atoms (that is, organic acids in which hydrogen atoms other than those of COOH groups are attached only to primary and/or secondary carbon atoms). Preferred solvents include lower aliphatic monocarboxylic acids having 2 to about 6 carbon atoms, more preferably acetic acid. Mixed solvents (including mixtures of solvents with inert diluents such as benzene) can, of course also be used. The amount of solvent used is selected so that less than 1.5 moles of solvent are present in the oxidation zone for each mole of the cycloaliphatic hydrocarbon. When oxidizing cyclohexane in acetic acid solvent, for example, this molar ratio range corresponds to a concentration of at least about 45–50 wt. % cyclohexane and no more than about 50–55 wt. % acetic acid, with the preferred relative quantities being about 60–90 wt. % cyclohexane and about 10–40 wt. % acetic acid. For cycloheptane or cyclooctane, which have higher molecular weights, the corresponding weight percentage of the cycloalkane will, of course, be greater than 48 wt. %, whereas for cyclopentane, the corresponding weight percentage will be less.

Suitable oxidation catalysts (d) are conventional in nature and include polyvalent heavy metal catalysts, especially those having atomic numbers from 23 to 29, as well as cerium. Particularly preferred catalysts are those containing cobalt, manganese, vanadium, and cerium and combinations thereof. These heavy metal catalysts are supplied to the oxidation zones in the form of compounds that are soluble or will become at least partially solubilized under the conditions of the oxidation reaction. Suitable such compounds include the oxides, hydroxides, and, preferably, the inorganic and organic salts of the metals. It is particularly preferred to use the catalyst metals as their acetates, naphthenates, and toluates, as well as various fatty acid salts, such as stearates, oleates, and the like.

The preferred catalysts include essentially any cobalt salt of an organic acid. Examples of suitable such catalysts include cobalt acetate, cobalt propionate, and cobalt naphthenate. Materials which form such cobalt salts in situ can also be employed. For example, cobalt oxide and acetic acid are suitable because they will form cobalt acetate in situ. It is particularly preferred for the cobalt salt to correspond to the salt of the acid which is used as the reaction solvent. Because acetic acid is the preferred solvent, cobalt(II) acetate is the most preferred catalyst.

The concentration of catalyst required within the oxidation zone is somewhat dependent on the desired rate of oxidation. Accordingly, preferred amounts of catalyst vary from about 0.005 to about 0.6 mole per 1000 grams of reaction mixture, more preferably between about 0.015 and about 0.3 mole per 1000 grams and most preferably between about 0.03 and about 0.2 mole per 1000 grams. Of course, substantially greater amounts of catalyst (for example, up to 1 mole per 1000 grams of reaction mixture or even more) can be employed, but the use of such large quantities provides little advantage and, in fact, the use of such large quantities can cause problems in recovery of catalyst for recycle and re-use.

It is not necessary to use extraneous promoters, initiators, and the like in the process of the invention. Such extraneous materials can give slightly improved rates and/or conversion and/or selectivities, but their use generally increases cost and may result in the formation of by-product. Thus, such additives are normally not used. However, if special circumstances warrant their use, it is possible to use extraneous promoters such as, for example, acetaldehyde, methyl ethyl ketone, cyclohexanol, cyclohexanone, and the like.

The process of this invention involves a single-stage oxidation that subjects a high concentration of the saturated cycloalkane to mild oxidation conditions, one of the important features being the intentional limitation of the extent of conversion of the cycloalkane. As used herein, the term "conversion" refers to the ratio (usually expressed as a percentage) of the quantity of cycloalkane that reacts in any manner to the quantity of cycloalkane in the feedstock. Stated another way with reference to oxidation products and by-products, the term "conversion" refers to the total moles of all dibasic acids produced (for example, the sum of adipic acid, glutaric acid, and succinic acid prepared when oxidizing cyclohexane) and the various by-products to the moles of the cycloalkane in the feedstock.

Reaction conversion will increase with reaction time to yield a higher concentration of dibasic acids. However, it is preferable to limit the extent of conversion because the dibasic acid products are subject to further oxidation and thus a loss of selectivity. For example, when the feed cyclic alkane is cyclohexane, the primary product is adipic acid. However, as the conversion of cyclohexane increases, the selectivity to adipic acid diminishes. Therefore, it is preferable for the average concentration of adipic acid to be kept at the lowest practical level consistent with recovery costs. Furthermore, since free radical oxidation attacks all oxidizable species in proportion to both reactivity and concentration, the presence of high concentrations of cyclohexane redirects the oxidation away from adipic acid toward cyclohexane, thereby minimizing post-oxidative attack on adipic acid. Low adipic acid and high cyclohexane concentrations in the oxidation zone (or, expressed alternately, low conversion) will maximize selectivity. Low conversion can sometimes have negative economic effects but is essentially without economic consequence in the high cyclohexane system of this invention, because the desired adipic acid product is facilely and economically precipitated and removed from the system as a solid. In the practice of the present invention, conversion per pass of cyclohexane is limited to the range of from about 7% to no more than about 30%. Although higher conversions are achievable, adipic acid selectivities tend to deteriorate. In the preferred embodiments of the present invention, conversions are preferably kept at 10% to 30%, most preferably 15 to 25%, per pass.

Reaction temperatures can vary from about 60° to about 175° C., with preferred temperatures being from 90° to 125° C. Temperatures below about 75° C. tend to result in undesirably low production rates of dibasic acids, whereas temperatures above about 150° C. tend to cause an increase in decarboxylation reactions (with concomitant release of $CO_2$). Accordingly, temperatures in the oxidation zone are preferably from 75° to 150° C. and most preferably from 90° to 125° C.

In contrast to the relatively precise temperature requirements, total pressure is generally not critical so long as it is sufficient to maintain a liquid phase. However, economic considerations associated with design and construction of the oxidation equipment normally dictate the use of pressures of from about 1 to about 100 atmospheres absolute (preferably from about 1 to about 70 atmospheres absolute and more preferably from about 5 to about 40 atmospheres absolute). On the other hand, the partial pressure of oxygen (measured in the vent gases from the oxidation zone) should be at least about 0.10 atmospheres absolute and preferably at least 0.3 atmospheres absolute. Maximum oxygen partial pressure is dictated almost entirely by flammability considerations.

The reaction mixture is preferably well agitated to insure better contact of the reactants. Agitation can be provided by mechanical stirring devices optionally aided by the ebullition caused by the introduction of the oxygen-containing gas into the liquid reaction mixture.

The reaction time can vary from about ten minutes to about six hours (or even more), with preferred reaction times being about 0.25 to two hours.

The process of the present invention provides surprising economic benefits when oxidizing high concentrations of cyclohexane (or other cycloalkanes) at low conversions to adipic acid (or other dibasic acids). In particular, the process combines high rates of adipic acid production with excellent selectivity, two important factors that can affect raw material costs, as well as capital expenditures. A further benefit associated with using a high concentration of cyclohexane is facile recovery of adipic acid in high yields in comparison to known processes.

The advantageous results can be compared with processes that emphasize higher conversion and low cyclohexane concentrations. For example, U.S. Pat. No. 3,231,608 reports adipic acid production rates of 3.5 to 4.0 wt. % per hour and at efficiencies generally around 73 to 76 wt. %. (It may be noted that, because adipic acid is the primary product of cyclohexane oxidation that has the highest possible molecular weight, the unit "wt. percent" will be higher than the usual selectivity-indicating unit "mole percent". In general, therefore, the reported efficiencies will be from about 2.8 to as much as 5 percentage points lower on a mole percent basis.) K. Tanaka in *Chemtech*, 555-559 (1974), and in *Hydrocarbon Processing*, 53, 114-120 (1974), reports up to about 80% conversion of cyclohexane at low concentrations of about 1.7M in acetic acid (about 14 wt. %). G. N. Kulsrestha et al in *J. Chem. Tech. Biotechnol.*, 50, 57-65 (1991), reports 85% conversion using about 18 wt. % cyclohexane at adipic acid production rates of from less than 1 up to about 4 wt. %/hr at selectivities of from 70 to 77 mole %, with a directly recoverable amount of adipic acid of from about 10 to 30% of that produced, thus requiring burdensome workup and recovery.

The following examples further illustrate details for the advantageous process of the present invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are given as degrees Celsius.

EXAMPLES

Throughout the examples the following terms have the meanings indicated:

Conversion—The ratio (expressed as a percentage) of the total moles of dibasic acids (that is, the sum of adipic acid, glutaric acid, and succinic acid) and ultimate losses to the moles of cyclohexane in the feedstock.

Reaction Rate—The weight percent (based on the total liquid-phase reaction medium) of adipic acid produced per hour (based on an extrapolation of the actual amount produced in the time described in each example).

Selectivity to Adipic Acid—The ratio (expressed as a percentage) of the moles of adipic acid formed to the number of moles of cyclohexane reacted and which cannot be recovered or recycled. This term is indicative of ultimate yield when non-product can be recovered and recycled.

Selectivity to Dibasic Acids—The ratio (expressed as a percentage) of the moles of all dibasic acid formed to the number of moles of cyclohexane reacted and which cannot be recovered or recycled. This term is indicative of ultimate yield.

The following gas-liquid chromatography (GLC) method was used for analytical determinations. The GLC analyses were carried out using columns having a diameter of 0.125 inch (ca. 3.2 mm) and varying lengths were packed with PEG 20M (that is, polyethylene glycol having a molecular weight of about 20,000) as the liquid substrate and an 80-100 mesh CHROMOSORB W support (available from Supelco Inc.; CHROMOSORB is a trademark of Johns-Manville Corporation) and fitted with a thermal conductivity detector. Samples were prepared for GLC analysis by converting the carboxylic acids to methyl esters. The methyl esters were prepared by mixing the sample with a fixed amount of excess methanol and about 5-10 wt. % of predried AMBERLYST 15 sulfonic acid resin (available from Rohm and Haas Company) and then heating over a steam bath for about 1 hour. Analytical standards for adipic acid, glutaric acid, and succinic acid, acetic acid (as well as other components for which quantization was desired) were prepared by the same technique using mixtures of known quantities of the pure compounds in ratios approximating those of the test samples. For example, for oxidations using 40% acetic acid medium, the standard was prepared using a mixture of acetic acid, water, adipic acid, glutaric acid, and succinic acid in a weight ratio of 5:1.25:1:0.1:0.05 and six parts of methanol for each part of the mixture. When analyzing the isolated dibasic acids for impurities (for example, the amounts of glutaric and succinic acids in adipic acid isolates), the samples were prepared using 12 parts of methanol for each part sample. Although the diesters are in equilibrium with smaller quantities of the free acids and monoesters under these conditions, this method provided accurate and reproducible results.

Oxidations are characterized by a typical "S curve" in graphs having oxidation rate plotted along the ordinate (i.e., the y axis) and time plotted along the abscissa (i.e., the x axis). The lower portion of the S curve is a combination of chemical and physical characteristics, being both a combination of a chemical induction period and heatup to reaction temperature. The sloping portion of the S curve is usually nearly constant for the major portion of the oxidation and serves as a good indicator of the rate of oxidation. The slope of the curve bends downward to become the top of the S curve only with the occurrence of a substantial reduction in the reactants and/or other oxidation limiting factors (such as phase separation), with an attendant drop in oxidation rate.

For measurement purposes, the starting time in the oxidations described in the examples is taken as the intercept of the slope of the S curve with the x-time axis. Furthermore, it is preferred to quench the oxidation before the top of the S curve is reached. In the zone where phase separation is beginning to occur, a disproportionate amount of oxidation of the catalyst-rich polar phase is believed to occur. This phase is rich in adipic acid and low in cyclohexane, conditions conducive to post-oxidation of adipic acid and deterioration in selectivity. Furthermore, this phase of the oxidation is a controllable feature of the reaction through removal of some water of reaction.

Unless otherwise indicated, the following procedure was employed for the experimental runs in the examples. A reaction mixture was formed by dissolving the catalyst in the solvent, adding the charge stock (which was cyclohexane in all of the examples), and an initiator to a 500-ml 316 stainless steel reactor equipped with a rotating magnetic agitator. The reactor was then sealed and pressurized to 14 atmospheres absolute with a mixture of 50% oxygen gas and 50% nitrogen gas. The reaction mixtures were heated to the reaction temperature, and the progress of oxidation was measured by the pressure drop due to oxygen consumption. At a chosen point, the reaction was quickly quenched by cooling by about 20°–30° C. and then worked up. During handling, the reaction effluent was kept as warm as possible to minimize the loss of adipic acid, which crystallizes readily and is the component most easily "lost" during handling. The reaction product phase-separated cleanly even at warm temperatures. Upon cooling to room temperature, a major cyclohexane-containing upper phase (usually 40 to 65 vol. % of the total effluent) formed and could be recycled directly to oxidation. The lower polar phase represented the remaining 35 to 60 vol. % of the total effluent and consisted of both a liquid and solid phases. The polar phase was typically very rich in adipic acid, being as high as 40–60% adipic acid. Typically, adipic acid amounting to 65–85% of that present could be directly recovered by a filtration process without a workup or concentration step that would add not only to the cost for recovery but also to the chemical complexity created by further chemical reactions in the concentration. In the practice of this invention, a major portion of the mother liquor (about 50 to 90% from the polar phase) can be sent directly back to oxidation without being subjected to chemical modification.

The polar phase consists primarily of acetic acid, as well as the water generated during the reaction but not removed, low concentrations of cyclohexane, residual amounts of dissolved adipic acid, essentially all of the glutaric and succinic acids, cyclic and linear intermediates of all of the dibasic acids, and ester derivatives of all of the dibasic acids and the intermediates. The portion of the polar phase that can be subjected to further processing is somewhat variable, but at least 10% (preferably 20–25%) can be processed to remove the glutaric and succinic acids and, if not removed elsewhere, the water generated during the reaction. The polar phase that can be further processed thus represents only a small portion of the oxidation effluent (other than adipic acid), in contrast to essentially complete processing for the known high conversion processes.

In addition to superior reaction rates and selectivity, the process of the invention typically provides ease of processability and economical handling that become possible by the use of high concentrations of cyclohexane.

EXAMPLE 1

To the 500-ml 316 stainless steel reactor was added 16.25 g (193 mmole) of cyclohexane, 8.75 g (146 mmole) of acetic acid solvent, and 0.288 g (1.16 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 105° C. for 45 minutes. By a combination of actual recovery and analysis it was found that the rate of adipic acid production was 25.5 wt. %/hr based on the amount of the reaction mixture. The conversion of cyclohexane was 21.2%. The selectivity to adipic acid was 88.2 mole %, to glutaric acid was 6.2 mole %, and to succinic acid was 3.6 mole %. About 79% of the total adipic acid was recovered by direct filtration of the cooled oxidation effluent.

EXAMPLE 2

To the 500-ml 316 stainless steel reactor was added 12.5 g (149 mmoles) of cyclohexane, 12.5 g (208 mmoles) of acetic acid solvent, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 52 minutes. By a combination of actual recovery and analysis it was found that the rate of adipic acid production was 16.8 wt. %/hr based on the amount of the reaction mixture. The conversion of cyclohexane was 23.1%. The selectivity to adipic acid was 79.6 mole %, to glutaric acid was 10.6 mole %, and to succinic acid was 6.4 mole %. About 65% of the total adipic acid was recovered by direct filtration of the cooled oxidation effluent.

EXAMPLE 3

To the 500-ml 316 stainless steel reactor was added 17.0 g (202 mmoles) of cyclohexane, 8.0 g (133 mmoles) of acetic acid solvent, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 40 minutes. By a combination of actual recovery and analysis it was found that the rate of adipic acid production was 29.4 wt. %/hr based on the amount of the reaction mixture. The conversion of cyclohexane was 22.6%. The selectivity to adipic acid was 81.5 mole %. About 81% of the total adipic acid was recovered by direct filtration of the cooled oxidation effluent.

Comparison of Example 3 with Example 1 shows that a reduction in temperature (from 117° C. in Example 3 to 105° C. in Example 1) and an increase in the amount of catalyst (from 0.096 g in Example 3 to 0.288 g in Example 1), with the other parameters being held constant, enhances selectivity while giving only a slightly reduced adipic acid production rate and percent recovery.

Comparison of Example 3 with Example 2 shows that an increase in cyclohexane relative to acetic acid (from 12.5 g/12.5 g in Example 2 to 17.0 g/8.0 g in Example 3), with the other parameters being held constant, substantially enhances the adipic acid production rate.

EXAMPLE 4

To the 500-ml 316 stainless steel reactor was added 12.5 g (149 mmoles) of cyclohexane, 5.5 g (92 mmoles) of acetic acid solvent, 7.0 g of benzene, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 50 minutes. By a combination of actual recovery and analysis it was found that the rate of adipic acid production was 20.8 wt. %/hr based on the amount of the reaction mixture. The conversion of cyclohexane was 26.1%. The selectivity to adipic acid was 83.2 mole %, to glutaric acid was 9.7 mole %, and to succinic acid was 5.5 mole %. About 81% of the total adipic acid was recovered by direct filtration of the cooled oxidation effluent.

Comparison of Example 4 with Example 2 shows that the replacement of a portion of the acetic acid solvent with benzene (which does not form a coordination complex with the cobalt catalyst), with the other parameters being constant, increases the oxidation rate.

EXAMPLE 5

To the 500-ml 316 stainless steel reactor was added 12.5 g (149 mmoles) of cyclohexane, 12.0 g (200 mmoles) of acetic acid solvent, 0.50 g of ethanol, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 50 minutes. By a combination of actual recovery and analysis it was found that the rate of adipic acid production was 20.5 wt. %/hr based on the amount of the reaction mixture. The conversion of cyclohexane was 25.4%. The selectivity to adipic acid was 84.1 mole %. About 69% of the total adipic acid was recovered by direct filtration of the cooled oxidation effluent.

Comparison of Example 5 with Example 2 shows that the replacement of a portion of the acetic acid solvent with ethanol as a promoter, with the other parameters being held constant, increases the oxidation rate.

EXAMPLE 6

To the 500-ml 316 stainless steel reactor was added 12.5 g (149 mmoles) of cyclohexane, 12.0 g (200 mmoles) of acetic acid solvent, 0.50 g of cyclohexanol, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 35 minutes. By a combination of actual recovery and analysis it was found that the rate of adipic acid production was 26.9 wt. %/hr based on the amount of the reaction mixture. The conversion of cyclohexane was 21.8%. The selectivity to adipic acid was 87.2 mole %. About 68% of the total adipic acid was recovered by direct filtration of the cooled oxidation effluent.

Comparison of Example 6 with Example 2 shows that the replacement of a portion of the acetic acid solvent with cyclohexanol as a promoter, with the other parameters being held constant, increases the oxidation rate.

EXAMPLE 7

To the 500-ml 316 stainless steel reactor was added 15.0 g (178 mmoles) of cyclohexane, 10.0 g (167 mmoles) of acetic acid solvent, and 0.192 g (0.771 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 105° C. for 70 minutes. By a combination of actual recovery and analysis it was found that the rate of adipic acid production was 15.6 wt. %/hr based on the amount of the reaction mixture. The conversion of cyclohexane was 22.6%. The selectivity to adipic acid was 85.1 mole%. About 79% of the total adipic acid was recovered by direct filtration of the cooled oxidation effluent.

EXAMPLE 8

To the 500-ml 316 stainless steel reactor was added 15.0 g (178 mmoles) of cyclohexane, 10.0 g (167 moles) of acetic acid solvent, and 0.384 g (1.54 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 105° C. for 35 minutes. By a combination of actual recovery and analysis it was found that the rate of adipic acid production was 29.6 wt. %/hr based on the amount of the reaction mixture. The conversion of cyclohexane was 21.4%. The selectivity to adipic acid was 84.8 mole %. About 77% of the total adipic acid was recovered by direct filtration of the cooled oxidation effluent.

EXAMPLE 9

To the 500-ml 316 stainless steel reactor was added 18.5 g (220 mmoles) of cyclohexane, 6.5 g (108 mmoles)

of acetic acid solvent, and 0.024 g (0.096 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 1.5 hours. By a combination of actual recovery and analysis it was found that the rate of adipic acid production was 6.0 wt. %/hr based on the amount of the reaction mixture. The conversion of cyclohexane was 8.8%. The selectivity to adipic acid was 83.1 mole %. About 61% of the total adipic acid was recovered by direct filtration of the cooled oxidation effluent.

Example 9 shows that a low catalyst concentration reduces oxidation rate.

EXAMPLE 10

To the 500-ml 316 stainless steel reactor was added 18.5 g (220 mmoles) of cyclohexane, 5.25 g (87 mmoles) of acetic acid solvent, 1.25 g of methyl ethyl ketone, and 0.024 g (0.096 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for one hour. By a combination of actual recovery and analysis it was found that the rate of adipic acid production was 18.0 wt. %/hr based on the amount of the reaction mixture. The conversion of cyclohexane was 18.5%. The selectivity to adipic acid was 85.4 mole %. About 82% of the total adipic acid was recovered by direct filtration of the cooled oxidation effluent.

Comparison of Example 10 with Example 9 shows that although low catalyst concentration reduces oxidation rate, the addition of methyl ethyl ketone as a promoter gives good oxidation rates.

EXAMPLE 11

To the 500-ml 316 stainless steel reactor was added 15.0 g (178 mmoles) of cyclohexane, 10.0 g (167 mmoles) of acetic acid solvent, and 0.64 g (2.57 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 90° C. for 1.5 hours. By a combination of actual recovery and analysis it was found that the rate of adipic acid production was 13.9 wt. %/hr based on the amount of the reaction mixture. The conversion of cyclohexane was 24.3%. The selectivity to adipic acid was 86.0 mole %. About 74% of the total adipic acid was recovered by direct filtration of the cooled oxidation effluent.

Example 11 shows that a high catalyst concentration provides an acceptable oxidation rate even at a somewhat reduced temperature of 90° C.

EXAMPLE 12

To the 500-ml 316 stainless steel reactor was added 15.0 g (178 mmoles) of cyclohexane, 10.0 g (167 mmoles) of acetic acid solvent, and 1.15 g (4.62 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 90° C. for 40 minutes. By a combination of actual recovery and analysis it was found that the rate of adipic acid production was 23.4 wt. %/hr based on the amount of the reaction mixture. The conversion of cyclohexane was 19.7%. The selectivity to adipic acid was 87.2 mole %. About 72% of the total adipic acid was recovered by direct filtration of the cooled oxidation effluent.

Example 12 shows that a high catalyst concentration provides an acceptable oxidation rate (especially in comparison to Example 11) even at a somewhat reduced temperature of 90° C.

EXAMPLE 13

To the 500-ml 316 stainless steel reactor was added 17.0 g (202 mmoles) of cyclohexane, 8.0 g (133 mmoles) of acetic acid solvent, and 0.384 g (0.771 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 100° C. for 50 minutes. By a combination of actual recovery and analysis it was found that the rate of adipic acid production was 22.4 wt. %/hr based on the amount of the reaction mixture. The conversion of cyclohexane was 19.6%. The selectivity to adipic acid was 88.7 mole %. About 79% of the total adipic acid was recovered by direct filtration of the cooled oxidation effluent.

EXAMPLE 14

To the 500-ml 316 stainless steel reactor was added 18.75 g (223 mmoles) of cyclohexane, 6.25 g (104 mmoles) of acetic acid solvent, and 0.096 g (0.385 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 105° C. for two hours. By a combination of actual recovery and analysis it was found that the rate of adipic acid production was 11.3 wt. %/hr based on the amount of the reaction mixture. The conversion of cyclohexane was 23.4%. The selectivity to adipic acid was 87.1 mole %. About 86% of the total adipic acid was recovered by direct filtration of the cooled oxidation effluent.

EXAMPLE 15

To the 500-ml 316 stainless steel reactor was added 18.75 g (223 mmoles) of cyclohexane, 6.25 g (104 mmoles) of acetic acid solvent, and 0.24 g (0.96 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 95° C. for two hours. By a combination of actual recovery and analysis it was found that the rate of adipic acid production was 10.8 wt. %/hr based on the amount of the reaction mixture. The conversion of cyclohexane was 20.2%. The selectivity to adipic acid was 88.2 mole % to glutaric acid was 6.4 mole % and to succinic acid was 3.5 mole %. About 83% of the total adipic acid was recovered by direct filtration of the cooled oxidation effluent.

Examples 12 and 13, wa well as Examples 14 and 15, show that uniform results can be obtained by appropriate balancing of cyclohexane concentration, catalyst concentration, and temperature.

EXAMPLE 16

To the 500-ml 316 stainless steel reactor was added 15.0g (178 mmoles) of cyclohexane, 10.0 g (167 mmoles) of acetic acid solvent, and 0.384 g (1.542 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 110° C. for 15 minutes. By a combination of actual recovery and analysis it was found that the rate of adipic acid production was 54.3 wt. %/hr based on the amount of the reaction mixture. The conversion of cyclohexane was 18.0%. The selectivity to adipic acid was 83.6 mole %. About 72% of the total adipic acid was recovered by direct filtration of the cooled oxidation effluent.

EXAMPLE 17

To the 500-ml 316 stainless steel reactor was added 15.0 g (178 mmoles) of cyclohexane, 10.0 g (167 mmoles) of acetic acid solvent, and 0.256 g (1.028 mmole) of cobalt(II) acetate tetrahydrate, as well as 0.05 g of acetaldehyde as an initiator to avoid an induction period. The reactor was sealed and pressurized to a pressure of 14 atmospheres with a mixture of 50% $O_2$ and 50% $N_2$. The reaction was then carried out at 117° C. for 15 minutes. By a combination of actual recovery and analysis it was found that the rate of adipic acid production was 76.0 wt. %/hr based on the amount of the reaction mixture. The conversion of cyclohexane was 24.1%. The selectivity to adipic acid was 82.1 mole %. About 78% of the total adipic acid was recovered by direct filtration of the cooled oxidation effluent.

Examples 16 and 17 show that appropriate balancing of cyclohexane concentration at restricted conversions with catalyst concentration and temperature gives very high adipic acid production rates and excellent selectivities.

What is claimed is:

1. A process for the preparation of $C_5$-$C_8$ aliphatic dibasic acids by oxidation of corresponding saturated cycloaliphatic hydrocarbons comprising
   (1) reacting, at a cycloaliphatic hydrocarbon conversion level of between 7% and 30%,
   (a) at least one saturated cycloaliphatic hydrocarbon having from 5 to 8 ring carbon atoms in the liquid phase and
   (b) an excess, relative to cycloaliphatic hydrocarbon (a), of oxygen gas or an oxygen-containing gas mixture
   in the presence of
   (c) less than 1.5 moles of a solvent per mole of cycloaliphatic hydrocarbon (a), wherein said solvent comprises an organic acid containing only primary and/or secondary hydrogen atoms and
   (d) at least 0.002 mole per 1000 grams of reaction mixture of a polyvalent heavy metal catalyst; and
   (2) isolating the $C_5$-$C_8$ aliphatic dibasic acid.

2. A process according to claim 1 for the preparation of adipic acid from cyclohexane.

3. A process according to claim 1 wherein the cycloaliphatic hydrocarbon conversion level is between 15% and 25%.

4. A process according to claim 1 wherein component (a) additionally contains a substantially inert diluent that is not a saturated cycloaliphatic hydrocarbon.

5. A process according to claim 1 wherein component (b) is oxygen, air, or a mixture of oxygen and an inert gaseous diluent.

6. A process according to claim 1 wherein the partial pressure of oxygen over the reaction mixture is from 0.10 to 100 atmospheres absolute.

7. A process according to claim 1 wherein solvent (c) is acetic acid.

8. A process according to claim 1 wherein 0.1 to 1.0 moles of solvent are used per mole of cycloaliphatic hydrocarbon (a).

9. A process according to claim 1 wherein catalyst (d) is a cobalt salt of an organic acid.

10. A process according to claim 1 wherein catalyst (d) is cobalt(II) acetate.

11. A process according to claim 1 wherein 0.005 to 0.6 mole of catalyst per liter of reaction mixture are used.

12. A process according to claim 1 wherein 0.015 to 0.3 mole of catalyst per liter of reaction mixture are used.

13. A process according to claim 1 wherein the reaction is carried out at a temperature of from 60° to 175° C.

* * * * *